United States Patent [19]

Nadelson

[11] 4,035,494
[45] July 12, 1977

[54] BIS-P-PIVALOYL BENZYLAMINES

[75] Inventor: Jeffrey Nadelson, Lake Parsippany, N.J.

[73] Assignee: Sandoz, Inc., East Hanover, N.J.

[21] Appl. No.: 623,752

[22] Filed: Oct. 20, 1975

[51] Int. Cl.$^2$ ............... C07D 243/08; A61K 31/55
[52] U.S. Cl. .................. 424/244; 260/239 BC; 260/268 DK; 260/570.5 P; 424/250; 424/325
[58] Field of Search .............. 260/239 BC; 424/244

[56] References Cited

U.S. PATENT DOCUMENTS

| 3,093,631 | 6/1963 | Groo et al. | 424/244 |
|---|---|---|---|
| 3,098,066 | 7/1963 | Mull | 424/244 |
| 3,532,685 | 10/1970 | Arnold et al. | 260/239 BC |
| 3,869,459 | 3/1975 | Milkowski et al. | 260/239 BC X |

Primary Examiner—Donald G. Daus
Assistant Examiner—D. B. Springer
Attorney, Agent, or Firm—Gerald D. Sharkin; Robert S. Honor; Timothy G. Rothwell

[57] ABSTRACT

Bis-p-pivaloyl benzylamines, e.g. 4',4'''-[(N,N'-dimethyl-1,2-ethanediyldiimino)dimethylene]bis(-pivalophenone) are prepared by treating a sym-dimethylethylenediamine with a corresponding α-halo-p-pivaloyl toluene and are useful as hypolipidemic agents.

5 Claims, No Drawings

BIS-P-PIVALOYL BENZYLAMINES

This invention relates to bis-p-pivaloyl benzylamines which exhibit hypolipidemic activity, pharmaceutically acceptable salts thereof and to their preparation.

The compounds of this invention may be represented by the following structural formula:

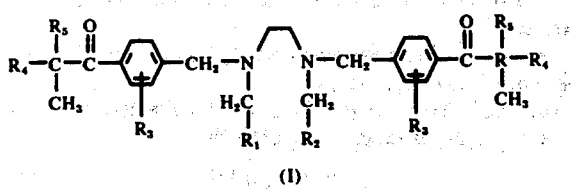

where
- $R_1$ and $R_2$ are both hydrogen, or together represent a direct bond or methylene, and
- $R_3$ represents hydrogen or halo having an atomic weight of about 19 to 36, i.e. fluoro or chloro, and
- $R_4$ and $R_5$ each independently represent lower alkyl having 1 to 2 carbon atoms, i.e. methyl or ethyl.

The compounds of formula (I) are prepared according to the following reaction scheme:

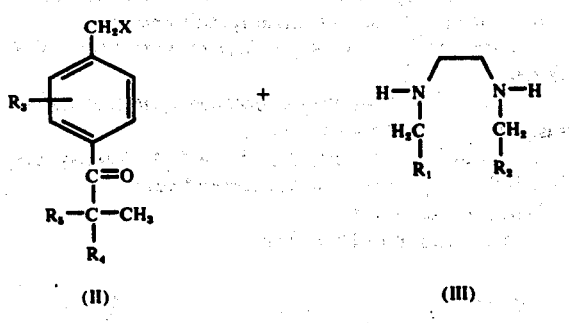

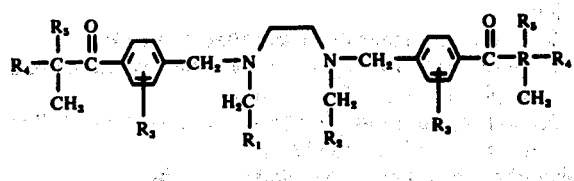

where
X is halo having an atomic weight of about 35 to 80, and
$R_1$, $R_2$, $R_3$, $R_4$ and $R_5$ are as defined above.

The compounds of formula (I) are prepared by treating a compound of the formula (II) with a compound of the formula (III) in a mole ratio of 2:1 to 2.5:1 respectively, in the presence of an acid binding agent such as pyridine, triethylamine, N,N-diisopropyl ethylamine and the like, preferably N,N-diisopropyl ethylamine in the presence of an inert organic solvent. Although the particular solvent employed is not critical, it is preferred that an aromatic hydrocarbon, such as benzene, toluene and the like, or a halogenated hydrocarbon such as methylene dichloride, chloroform and the like, be employed, preferably toluene. The temperature of the reaction is not critical, but it is preferred that the reaction be carried out at a temperature of from about 50° to 150° C., preferably at the reflux temperature of the solvent. The reaction may be run from about 12 to 30 hours, preferably from about 18 to 22 hours. The product is recovered using conventional techniques, e.g. filtration.

Many of the compounds of formulae (II) and (III) are known and may be prepared by methods described in the literature. The compounds of formula (II) and (III) not specifically described may be prepared by analogous methods from known starting materials.

The compounds of formula (I) are useful because they possess pharmaceutical activity in animals as hypolipidemic agents, as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 120 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, [345-347]) are added, and the mixture is shaken for one hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formula (I) may be similarly administered in the form of their non-toxic pharmaceutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The hypolipidemic effective dosage of these active compounds in the alleviation of lipidemia may vary depending on the particular compound employed and the severity of the condition being treated. However, in general, satisfactory results are obtained when the compounds of formula (I) are administered at a daily dosage of from about 10 milligrams to about 250 milligrams per kilogram of animal body weight, preferably given in divided doses two to four times a day, or in sustained release form. For most large mammals, the total daily dosage is from about 600 milligrams to about 3000 milligrams. Dosage forms suitable for internal use comprise from about 150 to about 1500 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
|---|---|
| 4',4'''-[(N,N'-dimethyl-1,2-ethanediyldiimino)dimethylene] bis (pivalophenone) | 150 |
| inert solid diluent (starch, lactose, kaolin) | 300 |

EXAMPLE I

4',4'''-[(N,N'-dimethyl-1,2-ethanediyldiimino)dimethylene]bis(pivalophenone)dihydrochloride.

To a mixture of 12.9 g. (0.10 mole) of N,N-diisopropylethylamine and 1.85 g. (0.021 mole) of sym-dimethylethylenediamine in 100 ml. of toluene, there is added dropwise 12.0 g. (0.047 mole) α-bromo-4-pivaloyl toluene in 100 ml. toluene. After the addition is complete, the resulting mixture is refluxed for 20 hours. The mixture is then cooled and filtered and the excess solvent removed in vacuo. The resulting oil is dissolved in ether and treated with 2N hydrochloric acid. The solid is filtered and washed with ether to give 4',4'''-[(N,N'-dimethyl-1,2-ethanediyldiimino)dimethylene]bis(pivalophenone)dihydrochloride; m.p. 280°–281° C.

Following the above procedure and using in place of α-bromo-4-pivaloyl toluene, an equivalent amount of a. α-bromo-2-fluoro-4-pivaloyl toluene, or b. α-bromo-2-chloro-4-pivaloyl toluene there is obtained a. 4',4'''-[(N,N'-dimethyl-1,2-ethanediyldiimino)-dimethylene]bis(3-fluoro-pivalophenone) or b. 4',4'''-[(N,N'-dimethyl-1,2-ethanediyldiimino)-dimethylene]bis(3-chloro-pivalophenone), respectively.

The 4',4'''-[(N,N'-dimethyl-1,2-ethanediyldiimino)-dimethylene]bis(pivalophenone) of this example is an effective hypolipidemic agent when orally administered to an animal suffering from lipidemia at a dosage of 150 mg. four times per day.

EXAMPLE II

4',4'''-[(1,4-piperazinediyl)dimethylene]bis(-pivalophenone)

To a mixture of 12.9 g. (0.10 mole) of N,N-diisopropylethylamine and 1.81 g. (0.021 mole) of piperazine in 100 ml. toluene there is added dropwise 12.0 g. (0.047 mole) of α-bromo-4-pivaloyl toluene in 100 ml. toluene. After the addition is complete, the resulting mixture is refluxed for 20 hours. The mixture is then cooled and filtered and the excess solvent removed in vacuo, to give 4',4'''-[(1,4-piperazinediyl)dimethylene]bis(pivalophenone); m.p. 161°–162.5° C.

Following the above procedure and using in place of α-bromo-4-pivaloyl toluene an equivalent amount of a. α-bromo-2-fluoro-4-pivaloyl toluene, or b. α-bromo-2-chloro-4-pivaloyl toluene there is obtained a. 4',4'''-[(1,4-piperazinediyl)dimethylene]bis (3-fluoro-pivalophenone), or b. 4',4'''-[(1,4-piperazinediyl)dimethylene]bis (3-chloro-pivalophenone) respectively.

EXAMPLE III

Following the procedure of Example 1, and using in place of sym-dimethylethylenediamine 2.10 g. (0.021 mole) of homopiperazine, there is obtained a. 4',4'''-[(1,4-homopiperazinediyl)dimethylene]-bis(pivolophenone)dihydrochloride; m.p. 266° to 267° C.

Again following the procedure of Example 1, and using in place of sym-dimethylenediamine an equivalent amount of homopiperazine and in place of α-bromo-4-pivaloyltoluene an equivalent amount of b. α-bromo-2-fluoro-4-pivaloyl toluene, or c. α-bromo-2-chloro-4-pivaloyl toluene there is obtained b. 4',4'''-[(1,4-homopiperazinediyl)dimethylene]-bis(3-fluoro-pivalophenone) or c. 4',4'''-[(1,4-homopiperazinediyl)dimethylene]-bis(3-chloro-pivalophenone) respectively.

What is claimed is:

1. A compound of the formula

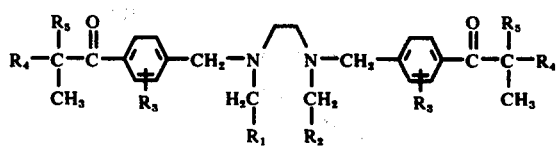

where $R_1$ and $R_2$ together represent methylene, and $R_3$ represents hydrogen or halo having an atomic weight of about 19 to 36, and $R_4$ and $R_5$ each independently represent lower alkyl having 1 to 2 carbon atoms, or a pharmaceutically acceptable salt thereof.

2. The compound of claim 2 which is 4',4'''-[(1,4-homopiperazinediyl)dimethylene]bis(pivalophenone).

3. The compound of claim 1 which is 4',4'''-[(1,4-homopiperazinediyl)dimethylene]bis(pivalophenone)-dihydrochloride.

4. A pharmaceutical composition comprising an amount of a compound of claim 1 effective in the treatment of lipidemia and a pharmaceutically acceptable diluent or carrier therefor.

5. A method of treating lipidemia which comprises administering to a mammal in need of said treatment a hypolipidemic effective amount of a compound of claim 1.

* * * * *